US009925014B2

(12) United States Patent
Robert et al.

(10) Patent No.: US 9,925,014 B2
(45) Date of Patent: *Mar. 27, 2018

(54) ACTUATOR AND DRIVE FOR MANIPULATING A TOOL

(71) Applicant: Titan Medical Inc., Toronto (CA)

(72) Inventors: Rene Robert, East Greenwich, RI (US); David Allen Zitnick, Providence, RI (US)

(73) Assignee: TITAN MEDICAL INC., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/442,070

(22) Filed: Feb. 24, 2017

(65) Prior Publication Data

US 2017/0156807 A1 Jun. 8, 2017

Related U.S. Application Data

(63) Continuation of application No. 15/294,477, filed on Oct. 14, 2016, now Pat. No. 9,629,688, which is a
(Continued)

(51) Int. Cl.
*A61B 34/00* (2016.01)
*A61B 34/30* (2016.01)
(Continued)

(52) U.S. Cl.
CPC ........ *A61B 34/70* (2016.02); *A61B 17/00234* (2013.01); *A61B 34/30* (2016.02);
(Continued)

(58) Field of Classification Search
CPC ... A61B 34/70; A61B 34/30; A61B 17/00234; F16C 1/12
See application file for complete search history.

(56) References Cited

U.S. PATENT DOCUMENTS 5,636,780 A * 6/1997 Green ............. A61B 17/07207
227/176.1
6,331,181 B1 * 12/2001 Tierney ................. G06Q 30/02
600/429
(Continued)

FOREIGN PATENT DOCUMENTS

EP 3203924 A2 8/2017

OTHER PUBLICATIONS

International Search Report for International Application No. PCT/CA2015/000098 dated Jul. 29, 2015, in 13 pages.
(Continued)

*Primary Examiner* — Zakaria Elahmadi
(74) *Attorney, Agent, or Firm* — Knobbe, Martens Olson & Bear, LLP

(57) ABSTRACT

A tool apparatus and a method for actuating a tool apparatus are disclosed. The tool apparatus includes an actuator housing, and an elongate tool manipulator extending outwardly from the actuator housing and having a plurality of control links extending along a length of the tool manipulator. The control links are operable to cause movement of a distal end of the tool manipulator in response to movement of the control links in an actuating direction generally aligned with the length of the tool manipulator. The apparatus also includes a plurality of actuators, each actuator being associated with at least one of the control links and being mounted in the actuator housing to facilitate a range of travel in a transverse direction substantially orthogonal to the actuating direction, and a plurality of linkages. Each linkage is associated with one of the control links and extends between the control link and the respective actuator and is operable to transmit drive forces between the actuator and the control link.

29 Claims, 7 Drawing Sheets

Related U.S. Application Data continuation of application No. PCT/CA2015/000098, filed on Feb. 18, 2015.

(60) Provisional application No. 62/090,798, filed on Dec. 11, 2014.

(51) Int. Cl.
*A61B 17/00* (2006.01)
*F16C 1/12* (2006.01)
*F16H 25/20* (2006.01)

(52) U.S. Cl.
CPC ...... *F16C 1/12* (2013.01); *A61B 2017/00367* (2013.01); *A61B 2017/00371* (2013.01); *A61B 2017/00477* (2013.01); *F16H 25/20* (2013.01)

(56) References Cited

U.S. PATENT DOCUMENTS

| | | | |
|---|---|---|---|
| 8,142,447 B2 | 3/2012 | Cooper et al. | |
| 2004/0193146 A1* | 9/2004 | Lee | A61B 17/062 606/1 |
| 2006/0235436 A1* | 10/2006 | Anderson | A61B 34/71 606/130 |
| 2008/0039255 A1* | 2/2008 | Jinno | A61B 17/062 474/148 |
| 2010/0274087 A1* | 10/2010 | Diolaiti | A61B 1/00087 600/118 |
| 2011/0290853 A1* | 12/2011 | Shelton, IV | A61B 17/07207 227/177.1 |
| 2011/0290855 A1* | 12/2011 | Moore | A61B 17/072 227/180.1 |
| 2011/0295242 A1* | 12/2011 | Spivey | A61B 17/07207 606/1 |
| 2012/0071752 A1* | 3/2012 | Sewell | A61B 6/12 600/424 |
| 2012/0298719 A1* | 11/2012 | Shelton, IV | A61B 17/07207 227/176.1 |
| 2014/0001231 A1* | 1/2014 | Shelton, IV | A61B 17/07207 227/175.3 |
| 2014/0001235 A1* | 1/2014 | Shelton, IV | A61B 17/07207 227/176.1 |
| 2014/0005653 A1* | 1/2014 | Shelton, IV | A61B 18/1442 606/33 |
| 2014/0005678 A1* | 1/2014 | Shelton, IV | A61B 17/07207 606/130 |
| 2014/0005703 A1* | 1/2014 | Stulen | A61B 17/29 606/169 |
| 2014/0276722 A1* | 9/2014 | Parihar | A61B 18/18 606/33 |
| 2014/0276931 A1* | 9/2014 | Parihar | A61B 17/32009 606/130 |
| 2014/0276950 A1 | 9/2014 | Smaby et al. | |
| 2016/0143633 A1* | 5/2016 | Robert | A61B 17/29 604/95.04 |
| 2016/0296219 A1* | 10/2016 | Srivastava | A61B 34/30 |
| 2017/0027656 A1 | 2/2017 | Robert et al. | |

OTHER PUBLICATIONS

Written Opinion for International Application No. PCT/CA2015/000098 dated Jul. 29, 2015, in 5 pages.
U.S. Appl. No. 14/899,768, filed Dec. 18, 2015, 2016/0143633 A1.
U.S. Appl. No. 15/294,477, filed Oct. 14, 2016, 2017/0027656 A1.

* cited by examiner

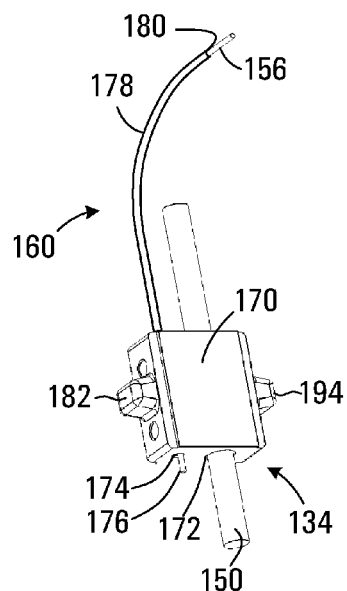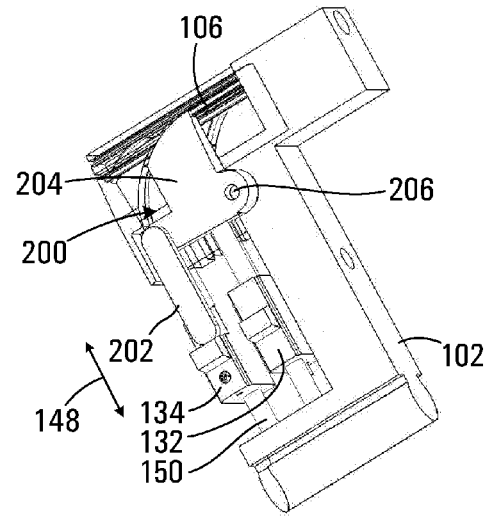
FIG. 3  FIG. 4
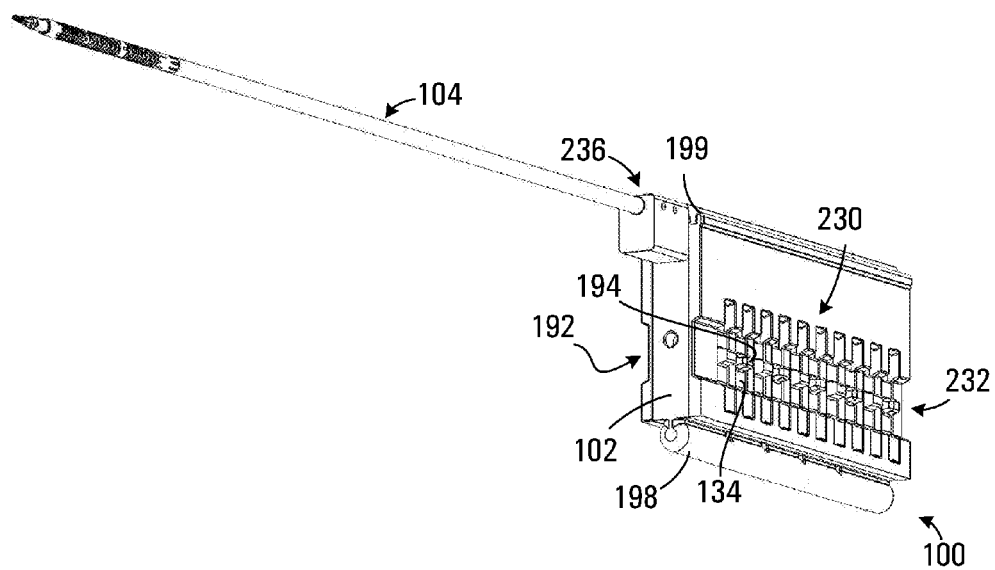
FIG. 5

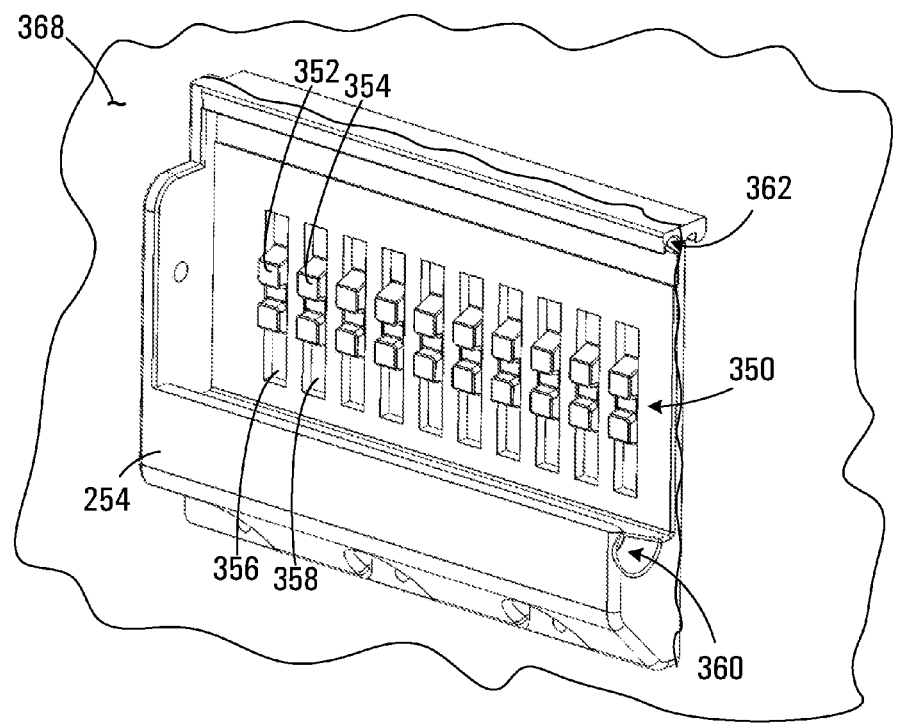
FIG. 10
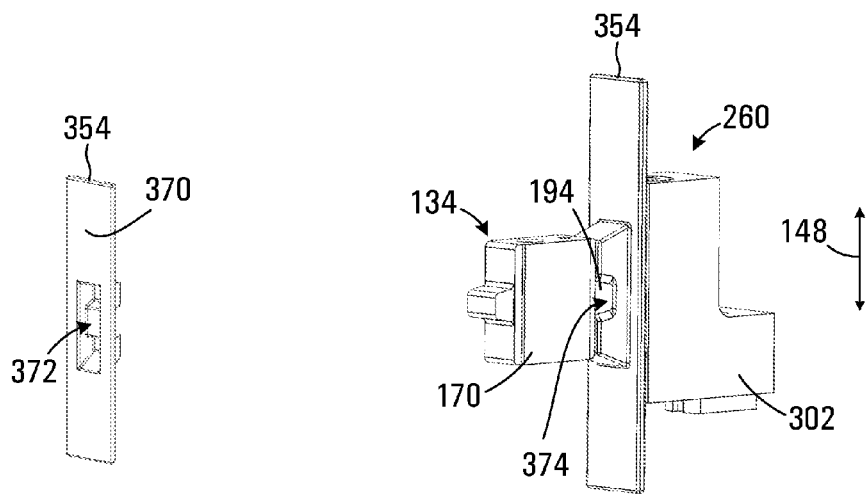
FIG. 11  FIG. 12

ACTUATOR AND DRIVE FOR MANIPULATING A TOOL

BACKGROUND OF THE INVENTION

1. Field of Invention

This invention relates to robotic manipulators and more particularly to an actuator and a drive for manipulating a tool.

2. Description of Related Art

Robotically actuated tools may be used in applications where there is an area of limited access for an operator. The robotically actuated tools may be inserted into the area of limited access and the operator may remotely manipulate the tool via one or more actuators and drivers, generally placed outside the area of limited access. However, while the actuators and drivers may be disposed outside the limited access area, there may still be constraints placed on their overall extent. Accordingly, there remains a need for actuators and drivers that are suitable for various robotically actuated tools, such as tools used in laparoscopic surgery.

SUMMARY OF THE INVENTION

In accordance with one disclosed aspect there is provided a tool apparatus including an actuator housing, an elongate tool manipulator extending outwardly from the actuator housing and having a plurality of control links extending along a length of the tool manipulator. The control links are operable to cause movement of a distal end of the tool manipulator in response to movement of the control links in an actuating direction generally aligned with the length of the tool manipulator. The apparatus also includes a plurality of actuators, each actuator being associated with at least one of the control links and being mounted in the actuator housing to facilitate a range of travel in a transverse direction substantially orthogonal to the actuating direction, and a plurality of linkages. Each linkage is associated with one of the control links and extends between the control link and the respective actuator and is operable to transmit drive forces between the actuator and the control link.

Each linkage may include a flexible length of the respective control link and the actuator housing may include a guide associated with each linkage that causes the flexible length of the control link to be curved through a generally circular arc between the tool manipulator and the respective actuator.

The guide may include an arcuate channel.

The apparatus may include a sheath covering the flexible length of the control link disposed within the channel, the sheath being operable to reduce friction between the control link and the channel.

Each linkage may further include a transition length extending in a direction generally aligned with the actuating direction, the transition length of each linkage having a length selected to cause successive ones of the plurality of actuators to be spaced along the actuator housing away from the elongate tool manipulator.

The guide may include a pulley.

Each linkage may include a lever coupled between the associated control link and the respective actuator, the lever being operably configured to pivot in response to movement of the actuator to cause movement of the control link.

The tool manipulator may include a rigid shaft portion and an articulated tool positioner operably configured to cause the movement of the distal end of the tool manipulator and the control link may include a substantially inflexible portion extending along the rigid shaft portion, and a flexible portion extending through the articulated tool positioner.

The actuator housing may include a plurality of parallel rails, each actuator being received on one of the parallel rails for guiding the actuator to provide the travel in the transverse direction.

The actuator housing may include a drive face and each actuator may include at least one drive engaging portion for receiving a drive force for moving the actuator, the at least one drive engaging portion being exposed on the drive face to facilitate coupling the actuator to a drive apparatus operable to provide the drive force.

The drive face may include a first drive face on a side of the actuator housing and may further include a second drive face disposed on an opposite side of the actuator housing and each actuator may include a first drive engaging portion exposed on the first drive face and a second drive engaging portion exposed on the second drive face, the first and second drive faces being operable to permit coupling of the actuator apparatus to a drive apparatus from either side of the actuator housing.

The tool manipulator may extend outwardly from a portion of actuator housing proximate an edge of the actuator housing such that the length of the tool manipulator is generally aligned with the edge of the housing.

Each actuator and respective linkage may be configured to place the associated control links in a relaxed condition when the actuator is disposed at a location within the actuator housing that is offset from a center of the range of travel of the actuator by a small proportion of the range of travel.

The control links may include at least one pair of control links associated with movements of the distal end of the tool manipulator in opposing directions within a common plane and the actuators associated with the pair of control links may be disposed in adjacent locations within the actuator housing.

The apparatus may include at least one tool connected to the distal end of the tool manipulator, the at least one tool providing functions controlled by at least one tool control link extending along the tool manipulator and the actuator housing may further include at least one tool actuator for controlling the at least one tool control link.

The tool control link may include at least one of a control link moveable in the actuating direction for actuating a jawed instrument and the plurality of actuators and linkages may include at least one actuator and a respective linkage for moving the control link in the actuating direction, and a tool control shaft for causing rotation of the tool about the distal end of the tool manipulator and the plurality of actuators and linkages may include at least one actuator and a respective linkage for transforming linear movement of the actuator into a rotating movement of the shaft.

The tool may be configured to operate in response to receiving an electrical actuation signal and the actuator housing may further include at least one input for receiving the electrical actuation signal, and a conduit extending through the housing for receiving an electrical cable for connecting the electrical signal between the input and the tool.

In accordance with another disclosed aspect there is provided a drive apparatus for providing a drive force to actuators of a tool apparatus as set forth above. The drive apparatus includes a chassis, a mounting interface for receiving the tool apparatus, and a plurality of drivers mounted side-by-side in the chassis, each driver corresponding to one of the plurality of actuators and having a drive coupling operable to move in the transverse direction for transmitting a drive force to one of the plurality of actuators when the tool apparatus is received at the mounting interface.

Each actuator of the tool apparatus may include at least one drive engaging portion and the drive coupling of each driver may be exposed on the mounting interface and disposed such that drive engaging portions on the tool apparatus interconnect with corresponding drive couplings when the tool apparatus is received at the mounting interface.

Each actuator and respective linkage of the tool apparatus may be configured to place the associated control links in a relaxed condition when the actuator is disposed at a location within the actuator housing that is offset from a center of the range of travel of the actuator by a small proportion of the range of travel and the drive coupling of each driver may be disposed to cause each respective drive engaging portion of the tool apparatus to be displaced from the center of the range of travel to place the associated control links in a pre-stressed condition when the tool apparatus is received at the mounting interface.

The mounting interface may include a slide interface configured to permit the tool apparatus to be received by sliding the actuator interface into engagement with the chassis in a direction generally aligned with the actuating direction, the drive engaging portions and corresponding drive couplings being aligned to permit the drive engaging portions to slide to interconnect with the respective drive couplings.

Each drive coupling of the plurality of drivers may include one of a protruding portion and a slot and each drive engaging portion of the plurality of actuators may include the other of a protruding portion and a slot.

The slide interface may be operably configured to provide sufficient retaining force in the transverse direction to prevent de-seating of the tool apparatus when transmitting drive forces, the retaining force being provided by at least one of static friction provided by contact forces between the drive engaging portions interconnecting with the corresponding drive couplings, actuation of at least one of the drivers causing movement of an associated drive coupling such that the plurality of drive couplings are no longer in alignment, thus preventing deseating of the tool apparatus, engagement of a detent operable to provide a sufficient retaining force in the actuating direction to prevent the tool apparatus sliding out of engagement with the mounting interface, and a fastener operable to provide a sufficient retaining force in the actuating direction to prevent the tool apparatus sliding out of engagement with the mounting interface.

Each driver may include a traversing element operably configured for movement in the transverse direction, and a rotating element coupled to the traversing element and being operable to cause traversing element to move in the transverse direction.

The rotating element may include a leadscrew and the traversing element may include a leadscrew nut coupled to the traversing element, the leadscrew nut being received on the leadscrew.

The apparatus may include a motor coupled to the rotating element for providing a rotational drive force.

The motor may provide a rotational drive force to rotating elements of at least two of the drivers, and the traversing elements of the at least two drivers may be configured for movement in opposing transverse directions for providing opposing drive forces to respective actuators of the tool apparatus, the opposing drive forces being operable to simultaneously cause pushing of one of the control links and pulling of another of the control links.

The motor may be mounted on a distal side of the chassis with respect to the tool manipulator.

In the event of a loss of power to the drive apparatus, each driver may be operably configured to maintain the drive coupling in a generally static location with respect to the chassis to prevent unintended movement of the distal end of the tool manipulator.

The mounting interface may include a removable barrier covering the chassis and plurality of drivers, the barrier having a plurality of intermediate couplers, the intermediate couplers being moveable in the transverse direction and being operable to transmit drive forces between the drive couplers of the drive apparatus and the respective drive engaging portions of the tool apparatus.

The removable barrier may be configured to receive a sterile drape for draping the drive apparatus.

In accordance with another disclosed aspect there is provided a method for actuating a tool apparatus, the tool apparatus including an elongate tool manipulator extending outwardly from an actuator housing and having a plurality of control links extending along a length of the tool manipulator, the control links being operable to cause movement of a distal end of the tool manipulator in response to movement of the control links in an actuating direction generally aligned with the length of the tool manipulator. The method involves receiving drive forces at a plurality of actuators, the plurality of actuators being mounted in the actuator housing to facilitate a range of travel in a transverse direction substantially orthogonal to the actuating direction. The method also involves transmitting the drive forces through a plurality of linkages, each linkage extending between one of the actuators and an associated control link, the transmitted drive forces causing movement of the associated control link in the actuating direction.

Receiving the drive forces may involve receiving drive forces from a plurality of drivers mounted side-by-side in a chassis, each driver corresponding to one of the plurality of actuators and having a drive coupling operable to move in the transverse direction for transmitting the drive force to the respective actuator.

The chassis may include a mounting interface and the method may involve slidably receiving the actuator in the mounting interface in a direction generally aligned with the actuating direction, the drive engaging portions and corresponding drive couplings being aligned to permit the drive engaging portions to slide to interconnect with the respective drive couplings.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 3 is a perspective view of one of a plurality of actuators and an associated linkage used in the tool apparatus shown in FIG. 1 and FIG. 2;

FIG. 4 is a perspective view of an alternative linkage embodiment;

FIG. 5 is a view of the tool apparatus shown in FIG. 1 from a different perspective viewpoint;

FIG. 10 is a view of a mounting interface of the drive apparatus shown in FIG. 6 from a different perspective viewpoint;

FIG. 11 is a view of a rear portion of an intermediate coupling of the mounting interface shown in FIG. 10;

FIG. 12 is a perspective view showing engagement between the tool apparatus shown in FIG. 1 and the drive apparatus shown in FIG. 7 in accordance with another embodiment.

DETAILED DESCRIPTION

Tool Apparatus

Figure 1:
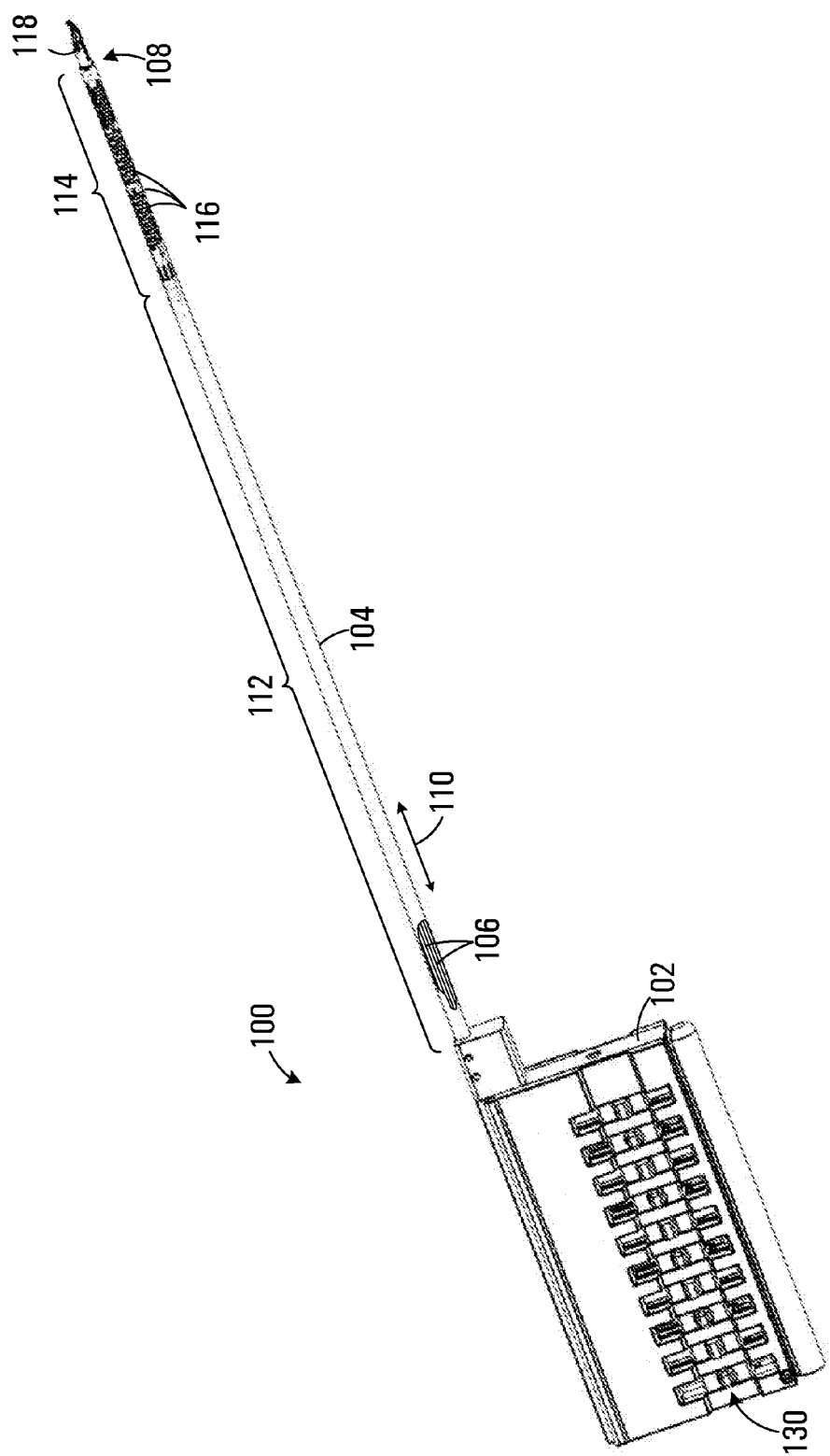
FIG. 1 is a perspective view of a tool apparatus according to a first embodiment.

Referring to FIG. 1, a tool apparatus according to a first embodiment of the invention is shown generally at 100. The tool apparatus 100 includes an actuator housing 102 and an elongate tool manipulator 104 extending outwardly from the actuator housing. The tool manipulator 104 includes a plurality of control links 106, shown in the partial cut-away on the tool manipulator. The plurality of control links 106 extend along a length of the tool manipulator 104 and are operable to cause movement of a distal end 108 of the tool manipulator in response to movement of the control links in an actuating direction. The actuating direction is generally aligned with the length of the tool manipulator and is indicated by the arrow 110. In one embodiment the control links 106 may each be a single flexible nitinol wire capable of about 200N in tension or compression without permanent deformation and capable of experiencing up to about 4% strain. Nitinol is an alloy of nickel and titanium having shape memory and superelasticity and its ability to support both tension and compression allows the control links 106 to be selectively pushed or pulled with similar forces without permanent deformation.

In the embodiment shown, the tool manipulator 104 includes a rigid shaft portion 112 and an articulated tool positioner 114 including a plurality of coupled guides 116. The plurality of coupled guides 116 are operable to move with respect to each other in response to pushing and/or pulling of the control links 106 causing the distal end 108 to assume various positions and orientations. An articulated tool positioner is described in detail in commonly owned patent application PCT/CA2013/001076 entitled "ARTICULATED TOOL POSITIONER AND SYSTEM EMPLOYING SAME". The tool manipulator 104 is configured to receive a tool 118, such as may be commonly used in laparoscopic surgery.

As disclosed above the plurality of control links 106 may be implemented using flexible wires such as nitinol. However, in other embodiments, the control links 106 may include an inflexible portion along the rigid shaft portion 112 since flexibility of the control links is not required along the rigid shaft, which would not bend significantly during operation. In such a case, the control links 106 may include an inflexible portion extending through the rigid shaft portion 112 and a flexible portion extending between the rigid shaft portion 112 and through the articulated tool positioner 114 to the distal end 108. The flexible and inflexible portions may be crimped, swaged, or welded together to form the control link 106.

Figure 2:
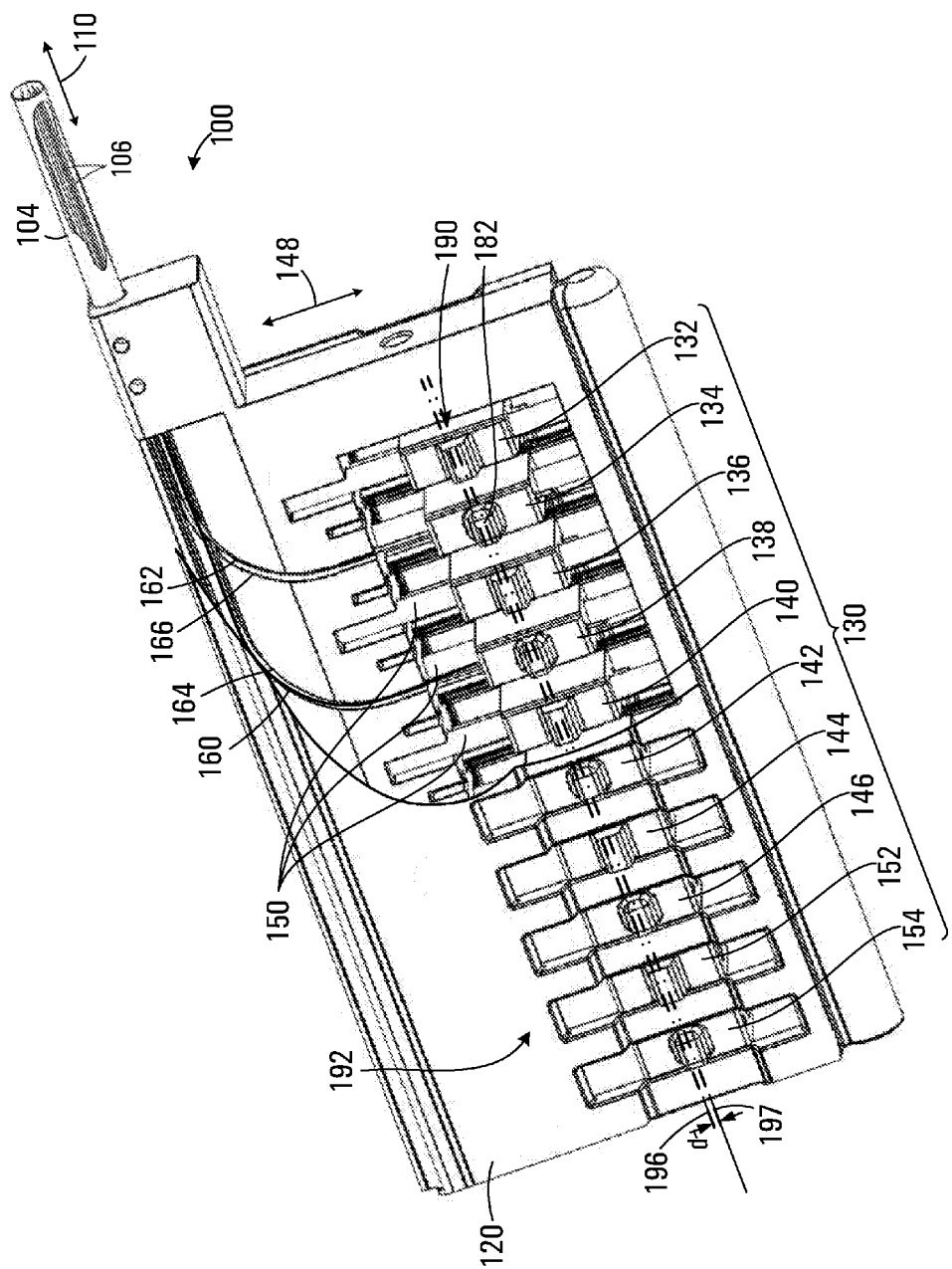
FIG. 2 is an enlarged perspective view of a portion of the tool apparatus shown in FIG. 1.

The actuator housing 102 and a portion of the tool manipulator 104 are shown in enlarged detail in FIG. 2. Referring to FIG. 2, the actuator housing 102 includes a cover plate 120, which is shown partially cut-away. The tool apparatus 100 includes a plurality of actuators 130. In this embodiment, the plurality of actuators 130 includes eight adjacently disposed actuators 132-146 for positioning the distal end 108 of the elongate tool manipulator 104. In this embodiment each of the actuators 132-146 is associated with a respective control link of the plurality of control links 106 and is mounted in the actuator housing 102 to facilitate a range of travel in a transverse direction. The transverse direction is substantially orthogonal to the actuating direction 110 and is indicated by the arrow 148. In the embodiment shown, each actuator 132-146 is received on one of a plurality of adjacently located parallel rails 150 extending in the transverse direction 148. The parallel rails 150 guide the respective actuators 132-146 for movement in the transverse direction 148. In other embodiments, the plurality of actuators 130 may include more or less than the eight actuators 132-146 shown in FIG. 2, depending on requirements for manipulating the distal end 108 of the tool manipulator 104.

In other embodiments a single actuator may be configured to actuate two control links. For example, two joined control link portions may be looped around a pulley such that movement of the actuator causes a pulling movement of one control link portion and a pushing movement of the other control link portion.

The plurality of actuators 130 may include further actuators 152 and 154 for controlling functions of the tool 118. For example, the tool 118 may be surgical scissors, forceps, or other jawed instrument that is operated by a tool control link extending along the length of the tool manipulator 104 and actuated by one of the actuators 152 or 154. The jaw of the tool 118 to be opened and closed in response to movement of the control link. Additionally, the tool 118 may also be rotatable about the distal end 108 and one of the actuators 152 and 154 may be used to actuate rotation of the tool through rotation of a tool control link such as a shaft extending along the length of the tool manipulator 104. In this embodiment the linkage associated with the tool control actuator may be configured to transform linear movement of the actuator into a rotating movement of the tool control shaft.

In other embodiments additional actuators may be provided as necessary for operating the tool 118. In some embodiments, the tool manipulator 104 may carry a tool such as a surgical cauterizer that is configured to operate in response to receiving an electrical actuation signal. The tool manipulator 104 may have a conduit extending through the actuator housing 102 for receiving an electrical cable and may also include an input connector for connecting the electrical actuation signal through the cable to the tool. The tool manipulator 104 may include a corresponding conduit for carrying the electrical cable between the housing and the tool. Alternatively, a conduit through the shaft may be omitted and the electrical cable may extend through the center of the shaft. In other embodiments where the shaft comprises an electrically conductive material, the shaft may be used as a first electrical conductor with a second electrical conductor being run along the tool manipulator to provide either the signal line or the ground return for the electrical actuation signal. In other cases a ground return may be provided through the patient's tissues and the conductive shaft may be sufficient to couple the electrical actuation signal to the tool 118.

The tool apparatus 100 further includes a plurality of linkages, of which linkages 160 and 162 are visible in FIG. 2. In the embodiment shown, the linkages are provided by a flexible length of one of the control links 106. For example, the linkage 160 comprises a length of one of the control links 106 and is associated with the actuator 138. The linkage 162 comprises a flexible length of another of the control links 106 and is associated with the actuator 134. As disclosed above, in some embodiments the control links 106 may be fabricated from a flexible material such as nitinol in which case the linkages 160 and 162 would be provided by a length of the flexible material. In other embodiments the control links 106 may have some flexible and some inflexible portions, and the linkages 160 and 162 may be provided by a further flexible length joined to the control link. The actuator housing 102 further includes channels 164 and 166 for receiving and guiding the respective lengths of the control links acting as linkages. The channels 164 and 166 each include an arcuate portion that guides the control link 106 through a generally circular arc between the actuator and the tool manipulator 104. The channels also include a straight portion extending through the actuator housing 102 in the actuating direction 110. Each of the linkages 160 and 162 are thus received within a respective channel and extend between one of the control links 106 and a respective actuator in the plurality of actuators 130. Other control links 106 are routed through respective arcuate channels on an opposite side of the actuator housing 102 (not shown in FIG. 2) to the actuators 132, 136, and 140. The linkages are operable to transmit forces between the associated actuator and control link.

The channels 164 and 166 are sized and toleranced to guide the respective linkages 160 and 162 without significantly constraining their movement within the channel. The control links 106 associated with each of the linkages and actuators in the plurality of actuators 130 have successively longer lengths selected to cause successive actuators to be spaced along the actuator housing 102 away from the tool manipulator 104. The additional length of the control links 106 for actuators in the plurality of actuators 130 that are spaced further away from the tool manipulator 104 does not introduce appreciable additional friction, since the additional lengths are guided by the straight portions of the channels 164 and 166.

Referring to FIG. 3, one of the plurality of actuators 130 (i.e. actuator 134) and the associated linkage 160 is shown in isolation. The actuator 138 includes a body 170 having an opening 172 for being received on the rail 150. The body 170 also includes an opening 174 for receiving and securing an end 176 of the control link 106 associated with the actuator 134. The linkage 160 is provided by a length 178 of the control link 106 that is curved through a generally circular arc and terminates in the opening 174. In this embodiment, the linkage 160 further includes a sheath 180 covering at least a portion of the length 178 that is disposed within the channel 164 (shown in FIG. 2). The sheath 180 may be a material such as Polytetrafluoroethylene (PTFE) that is operable to reduce friction between the linkage 160 and the channel 164.

Referring to FIG. 4, an alternative linkage embodiment actuated by the actuator 134 is shown generally at 200. The linkage 200 includes an arm 202 and a lever 204 received within the actuator housing 102. The lever 204 is mounted at a pivot point 206 and the control link 106 is attached to the lever. The arm 202 extends between the actuator 134 and the lever 204. When the actuator 134 is moved along the rail 150 in the transverse direction 148, the arm 202 causes the lever 204 to pivot about the pivot point 206 and a force is transmitted to the control link 106. A similar linkage to the linkage 200 would be provided on an opposite side of the actuator housing 102 for the actuator 132. In other embodiments, the linkage may be implemented using a pulley for guiding the control link 106 through the circular arc between the transverse direction 148 and the actuating direction 110.

Referring back to FIG. 3, the body 170 of the actuator 134 includes a drive engaging portion. The drive engaging portion 182 protrudes from the body 170 and is operable to receive a drive force for moving the body 170 along the rail 150. Referring back to FIG. 2, the actuators 130 each include respective drive engaging portions 190 similar to the drive engaging portion 182. The drive engaging portions 190 protrude outwardly beyond the cover plate 120 and are thus exposed to provide a drive face 192 on the actuator housing 102. The drive face 192 facilitates coupling of the plurality of actuators 130 of the tool apparatus 100 to a drive apparatus operable to provide the drive force. An embodiment of the drive apparatus is described later herein.

Referring to FIG. 5, the tool apparatus 100 is shown oriented with the drive face 192 obscured and in this embodiment the tool apparatus has a second drive face 230 disposed on an opposite side of the actuator housing 102 to the drive face 192. Referring back to FIG. 3, the body 170 includes a second drive engaging portion 194 extending from an opposite side of the body 170 to the drive engaging portion 182. Referring again to FIG. 5, the drive face 230 includes a second plurality of drive engaging portions 232 including the second drive engaging portion 194 associated with the actuator 134. The first drive face 192 and the second drive face 230 are substantially identical and permit the tool apparatus 100 to be driven via either the first or the second drive face. The tool manipulator 104 also extends outwardly from a portion 234 of actuator housing 102 that is proximate to an edge 236 of the actuator housing such that the length of the tool manipulator 104 is generally aligned with the edge. Together with the substantially identical drive faces 192 and 230, mounting the elongate tool manipulator 104 proximate the edge of the actuator housing 102 provides options for mounting the tool apparatus 100 in different orientations, as described later herein.

Referring back to FIG. 2, in the embodiment shown, the plurality of actuators 130 and the associated linkages 160 are configured to place the control links 106 of the tool manipulator 104 in a relaxed condition when the actuators are disposed at a location within the actuator housing 102 that is offset from a center of the range of travel of the actuator (indicated by line 196) by a distance d. As described later herein, during the process of loading the tool apparatus 100 the actuators 130 may be subsequently displaced from the offset location to align with the line 196 causing the actuators to align along the line 196, and placing the control links 106 in a pre-stressed tension condition. In one embodiment the offset d is selected to be a small proportion of the range of travel of the actuators 130 (about 0.5 mm).

Drive Apparatus

Figure 6:
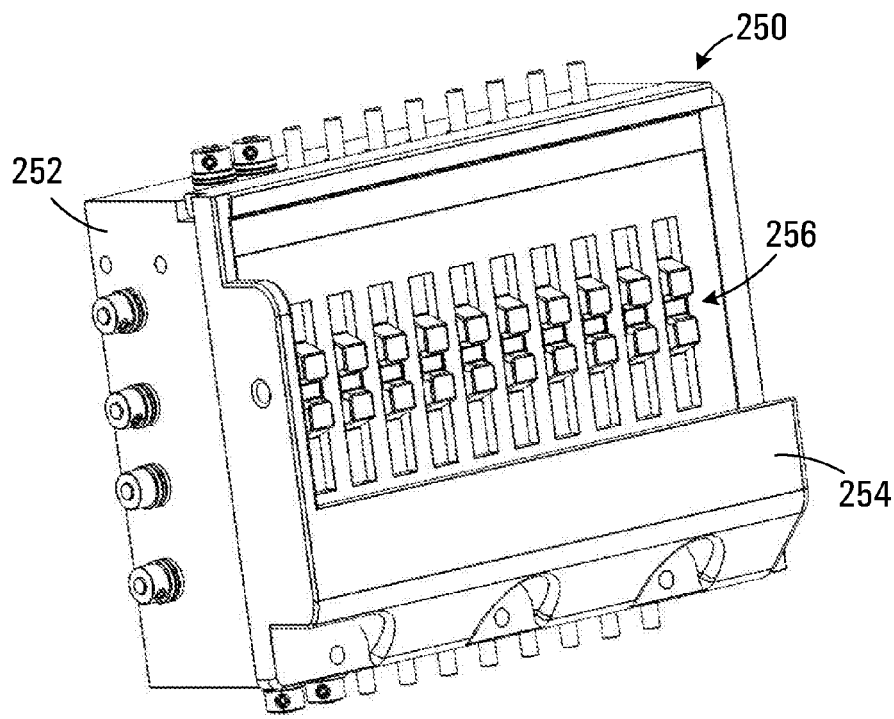
FIG. 6 is a perspective view of a drive apparatus for use with the tool apparatus shown in FIG. 1.
Figure 7:
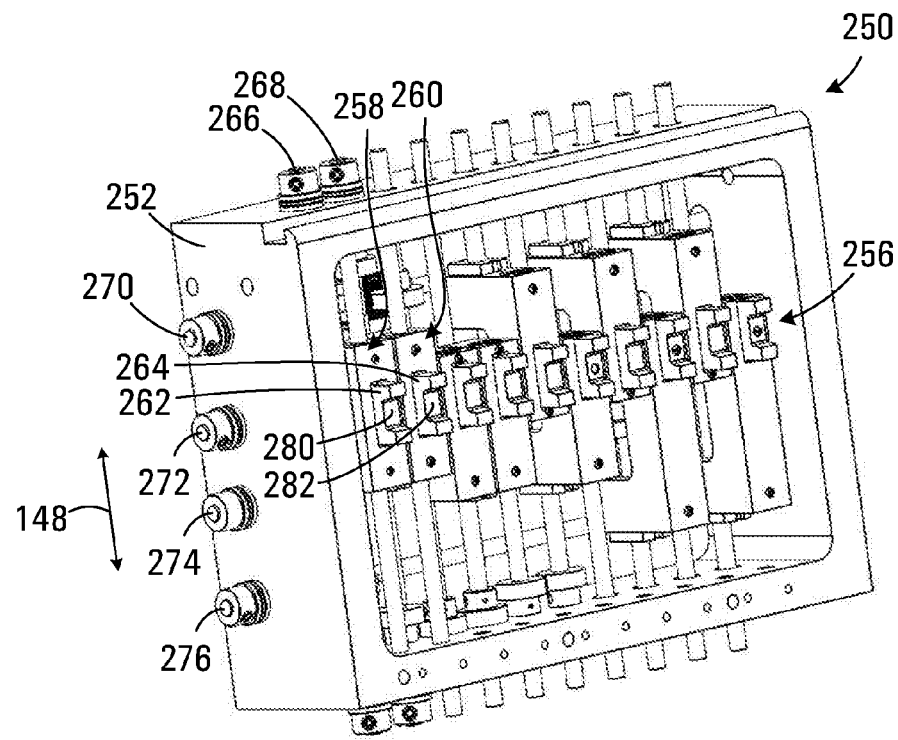
FIG. 7 is a perspective view of a chassis of the drive apparatus shown in FIG. 6.

Referring to FIG. 6, a drive apparatus for providing a drive force to actuators 130 of the tool apparatus 100 (shown in FIG. 1) is shown generally at 250. The drive apparatus 250 includes a chassis 252 and a mounting interface 254 for receiving the tool apparatus 100. The chassis 252 is shown in FIG. 7 with the mounting interface 254 removed. Referring to FIG. 7, the drive apparatus 250 includes a plurality of drivers 256 mounted side-by-side in the chassis 252. Each driver in the plurality of drivers 256 corresponds to one of the plurality of actuators 130 on the tool apparatus 100. Two exemplary drivers of the plurality of drivers 256 are indicated at 258 and 260 in FIG. 7, and respectively correspond to the actuators 132 and 134 on the tool apparatus 100. The drivers 258 and 260 each include respective drive couplings 262, 264, which are operable to move in the transverse direction for transmitting a drive force to the drive engaging portions 232 and 234 of the actuators 130 when the tool apparatus is received in the mounting interface 254.

Figure 8:
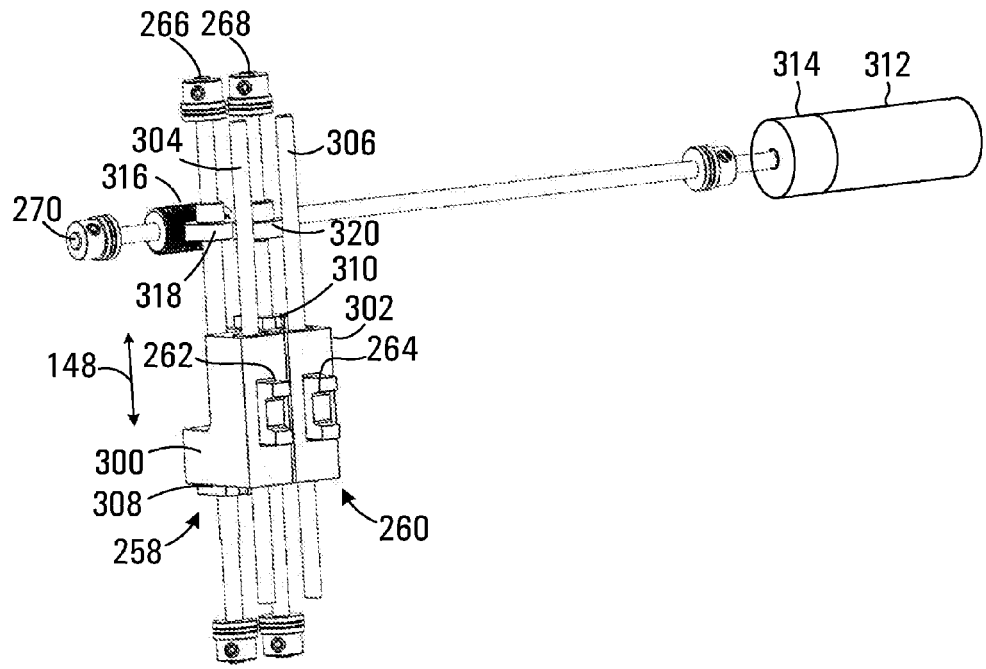
FIG. 8 is a perspective view of a pair of drivers shown in FIG. 7.

Each driver in the plurality of drivers 256 includes a rotating element in the form of a leadscrew 266, 268 extending in the transverse direction 148. In this embodiment, the drive apparatus 250 also includes a drive shaft for each pair of drivers (In FIG. 7, a drive shaft 270 is associated with the pair of drivers 258, 260). Components of the pair of drivers 258 and 260 are shown removed from the chassis in FIG. 8. Referring to FIG. 8, the drivers 258 and 260 each include a traversing element 300 and 302 received on respective rails 304 and 306. The rails 304, 306 extend in the transverse direction 148 and permit movement of the traversing elements 300 and 302 in the transverse direction. The leadscrews 266, 268 are threadably coupled to leadscrew nuts 308 and 310, which are coupled to the respective traversing elements 300 and 302. Rotation of the leadscrew 266 causes motion of the traversing element 300 along the rail 304 and rotation of the leadscrew 268 causes motion of the traversing element 302 along the rail 306. The drive shaft 270 is coupled to a motor 312 for providing a rotational drive force. In this embodiment, the motor 312 includes an encoder 314 for controlling rotational movement of the motor. The drive shaft 270 also includes a worm gear 316 disposed to engage a corresponding gear 318 on the leadscrew 266 for driving the leadscrew. The gear 318 on the leadscrew 266 engages a corresponding gear 320 and transmits the rotational drive to the leadscrew 268. The rotational drive imparted to the leadscrew 266 is thus in an opposite direction to the rotational drive imparted to the leadscrew 268, causing the traversing elements 300 and 302 to move in different transverse directions along the rails 304 and 306. The motor 312 thus provides a rotational drive force to rotating elements of at least two of the drivers configured for movement in opposing transverse directions. The opposing drive forces provided to adjacently located actuators 130 of the tool apparatus 100 are operable to simultaneously cause pushing of one of the control links 106 and pulling of another of the control links.

In the embodiment shown in FIG. 8, the motor 312 is mounted such that it would be on a distal side of the chassis 252 with respect to the tool manipulator 104. Mounting the motor 312 extending away from the rear of the chassis 252 has an advantage of removing elements from the vicinity of the tool manipulator 104 so as not to obstruct the portions of the apparatus that are closest to the surgical site.

In the event of a loss of power to the drive apparatus 250, friction associated with the gears and other elements of the drivers 258 and 260 would tend to cause the drive couplings 262 to be immobilized within the chassis 252. The distal end 108 of the tool manipulator 104 would thus also be immobilized preventing unintended movement of the distal end 108 of the elongate tool manipulator 104 and thus preventing the tool 118 from injuring the patient.

Referring back to FIG. 7, in the embodiment shown the six drivers of the plurality of drivers 256 that are adjacent to the pair of drivers 258, 260 are each paired with another driver and coupled to one of the shafts 272, 274, and 276, which are in turn coupled to respective motors (not shown in FIG. 7). In this embodiment, rotational drive is thus provided by four motors each motor driving a pair of drivers in the plurality of drivers 256. The remaining two drivers located furthest away from the drivers 258 and 260 are associated with driving the actuators 152 and 154 for controlling functions of the tool 118 and may be configured as required for the tool mounted on the tool manipulator 104.

The configuration shown in FIG. 7 is suitable for actuating a tool manipulator 104 having pairs of control links 106 associated with movements of the distal end 108 of the tool manipulator in opposing directions within a common plane. For example, with reference to FIG. 1, in one embodiment side-to-side movement of the distal end 108 in one may be associated with pushing one link of a pair of control links 106 while pulling another link of the pair. The push/pull actuation of pairs of control links provides a smooth movement by applying two separate actuation forces to move the articulated tool positioner 114. The push/pull actuation of pairs of control links also provides some redundancy should one of the control links fail during an operation since a single actuated link is sufficient to cause movement of the distal end 108 articulated tool positioner 114, such as the side to side movement described above.

Opposing transverse movements of the drivers that are coupled via the actuators 130 to the respective pairs of control links may thus actuate the side-to-side movement. In this embodiment, the opposing movements are provided by the drive apparatus 250 thus simplifying the tool apparatus 100. In use, a robotic surgery apparatus may include two or more units of the drive apparatus 250 for simultaneously driving two or more units of the tool apparatus 100. However, several differently configured tool apparatuses 100 having different tools 118 may be used during a surgery procedure and thus moving the opposing drive provisions to the drive apparatus 250 reduces overall system complexity. Alternatively, in another embodiment (not shown) the opposing movements may be provided within the tool apparatus 100.

In other embodiments movements to one side may be actuated by pulling only one of the control links while movement to the other side is associated with pulling the other control link. Alternatively, a single link can be implemented that causes movement to one side by pulling the control link and movement to the other side by pushing the control link.

Figure 9:
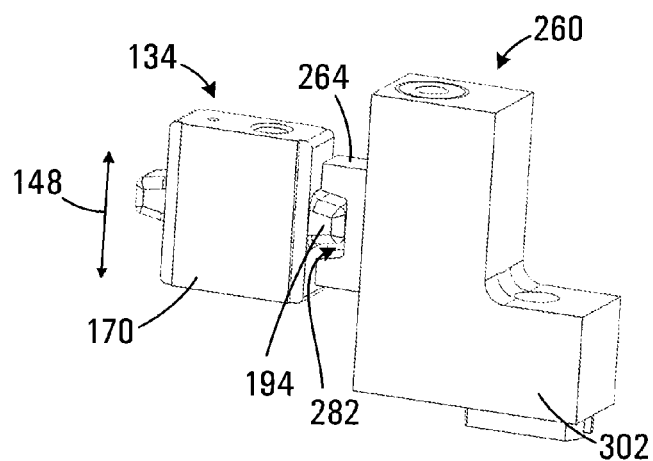
FIG. 9 is a perspective view showing engagement between the tool apparatus shown in FIG. 1 and the drive apparatus shown in FIG. 7 in accordance with one embodiment.

In the embodiment shown in FIG. 7, the plurality of drivers 256 each include slots, of which two slots 280 and 282 are indicated. The slots 280 and 282 are sized to receive the drive engaging portions 182 or 194 of the actuators 130 on the tool apparatus 100. Referring to FIG. 9, the traversing element 302 of the driver 260 and the body 170 of the actuator 134 are shown in an engaged state. The second drive engaging portion 194 of the actuator 134 engages the slot 282 in the drive coupling 264 of the driver 260. Movement of the drive coupling 264 in the transverse direction 148 imparts a drive force to the second drive engaging portion 194 causing movement of the actuator 134. The slot 282 is dimensioned to provide sufficient engagement between the drive engaging portion 194 and slot 282 when transmitting drive forces. In an alternative embodiment (not shown) the protruding portion may be on the driver 260 and the slot may be on the actuator 134.

The mounting interface 254 (shown in FIG. 6) is shown from a different perspective in FIG. 10. Referring to FIG. 10, in the embodiment shown the mounting interface 254 includes a plurality of intermediate couplers 350, including intermediate couplers 352 and 354. The intermediate couplers 350 are received in respective slots 356 and 358 in the mounting interface 254. Each of the plurality of intermediate couplers 350 have a shape that generally corresponds to the shape of the drive couplings (i.e. the drive couplings 262 and 264 shown in FIG. 7). Referring to FIG. 11, the intermediate coupler 354 is shown in rear view, and includes a sliding portion 370 received within the slot 358. The intermediate coupler 354 also includes a receptacle portion 372, shaped to receive the drive coupling 264. Referring to FIG. 12, the intermediate coupler 354 is shown in engagement between the traversing element 302 of the driver 260 and the body 170 of the actuator 134. The intermediate coupler 354 includes a drive coupling including a slot 374, which is shaped to receive the second drive engaging portion 194 on the body 170 of the actuator 134.

In operation, the intermediate coupler 354 slides within the slot 358 in the transverse direction 148 and thus provides an additional interface between the driver 260 and the actuator 134. The plurality of intermediate couplers 350 together with the mounting interface 254 act as part of a sterile barrier between the drive apparatus 250 and the tool apparatus 100. In one embodiment, the mounting interface 254 is provided as a removable barrier, which may be secured to the chassis 252 when setting up for a surgical procedure. The removable barrier may be provided in a sterile packaging, either for a single-use or for re-use after sterilization. In other embodiments, a sterile drape 368 may be attached around a perimeter of the mounting interface 254. The sterile drape is used to cover the chassis 252 of the drive apparatus 250 and other portions of a surgical apparatus, which the drive apparatus is coupled to.

Referring back to FIG. 10, the mounting interface 254 includes a first slot 360 and a second slot 362. The slots 360 and 362 have a generally cylindrical profile and are configured to provide a slide interface for receiving corresponding portions of the tool apparatus 100. Referring back to FIG. 5, in the embodiment shown the tool apparatus 100 includes a generally cylindrical portion 198 corresponding to the first slot 360 and a further generally cylindrical portion 199 corresponding to the second slot 362. The slots 360, 362, and cylindrical portions 198, 199 facilitate mounting of the tool apparatus 100 on the mounting interface 254 of the drive apparatus 250 while simultaneously engaging the cylindrical portions in the slots as the tool apparatus is slid into engagement.

Figure 13A:
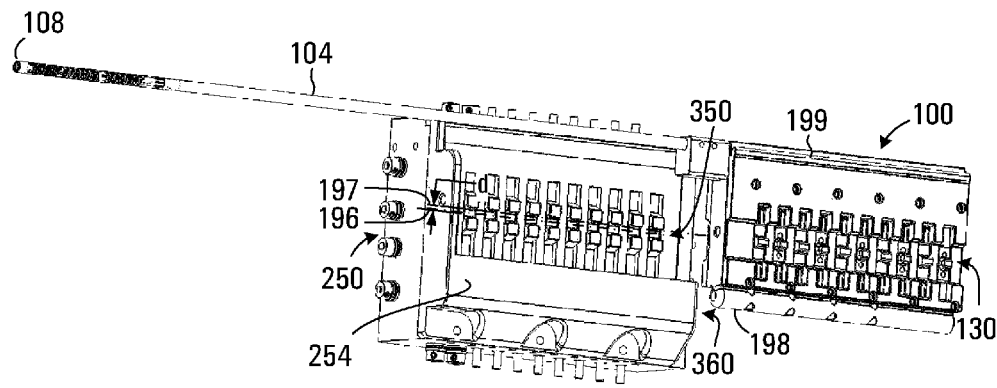
FIG. 13A-13C are a series of perspective views depicting a mounting process for engaging the tool apparatus shown in FIG. 1 in the drive apparatus shown in FIG. 6.
Figure 13B:
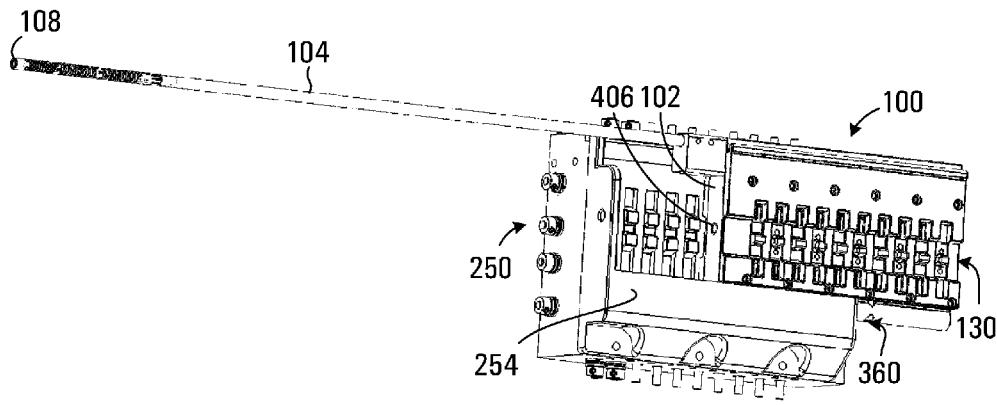
Figure 13C:
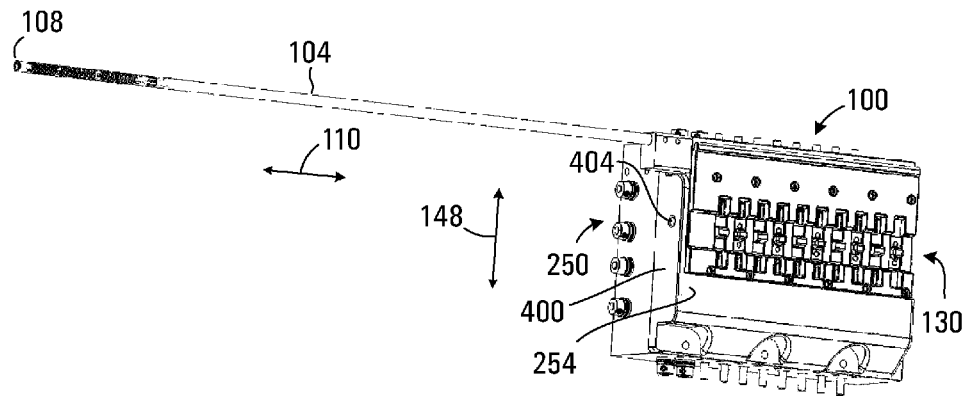

The engagement process is described further with reference to FIGS. 13A, 13B and 13C. Referring to FIG. 13A, initially the tool apparatus 100 is aligned with the drive apparatus 250 such that the portions 198 and 199 align with the respective slots 360 and 362 (shown in FIG. 10, slot 362 is not shown in FIG. 13A as it is obscured by the tool manipulator 104). The plurality of drivers 256 (not shown) of the drive apparatus 250 are actuated to each line up each of the plurality of intermediate couplers 350 at a center of their respective range of travel in the transverse direction 148. The driver alignment may be initiated by a computer controller (not shown) associated with the drive apparatus 250. The tool apparatus 100 is then slid into engagement with the mounting interface 254 of the drive apparatus 250.

Referring to FIG. 13B, as the tool apparatus 100 engages the mounting interface 254, the drive engaging portions 190 of the actuators 130 successively slide through the respective slots (374 in FIG. 11) of the plurality of intermediate couplers 350. As noted above in connection with FIG. 2, the actuators 130 may be located at a location 197 that is offset from a center of the range of travel 196, and as the drive engaging portions 190 of the actuators 130 successively slide through the actuator slots, each actuator is offset by the distance d placing the control links 106 in tension. Since the drivers 256 and intermediate couplers 350 have been aligned with the center line 196, the tool apparatus 100 is able to slide along the slots 360, 362 under relatively little applied force while simultaneously tensioning the plurality of control links 106.

Referring to FIG. 13C, the mounting interface 254 includes a stop plate 400 that engages a portion 402 of the actuator housing 102 (shown in FIG. 13B) when the plurality of actuators 130 of the tool apparatus 100 are each aligned with a corresponding one of the plurality of intermediate couplers 350. In this condition, the drive engaging portions 190 (as shown in FIG. 2) of the plurality of actuators 130 interconnect with the corresponding plurality of intermediate couplers 350. In the embodiment shown, the actuator housing 102 has a threaded opening 406 (FIG. 13B) and the stop plate 400 has a corresponding opening for receiving a retainer screw (not shown) for retaining the tool apparatus 100 in the mounting interface 254.

One advantage associated with the sliding engagement provided by the slots 360, 362 and the corresponding portions 198 and 199 (as shown in FIG. 10) is that the tool apparatus 100 is securely mounted to withstand operating forces in the transverse direction 148. The slide interface of the mounting interface 254 thus provides a sufficient retaining force in the transverse direction 148 to prevent deseating of the tool apparatus while transmitting drive forces to the plurality of control links 106. Forces on the tool apparatus 100 in the actuating direction 110 during operation will be minimal and the tool apparatus will be adequately restrained by without the need for external retaining means. The drive apparatus 250 also includes inherent features that prevent the tool apparatus 100 from sliding out of engagement with mounting interface 254. When the actuators 130 of the tool apparatus 100 are actuated and the elongate tool manipulator 104 is articulated, sufficient contact forces would be present in the direction 148 to cause static friction that would prevent motion of the apparatus in the actuating direction 110 (FIG. 13C). In addition, when any of the actuators 130 are actuated to locations away from the center line 196 (shown in FIG. 13A) and are thus not in alignment with one another, the actuator will act as a physical stop preventing motion of the instrument in the actuating direction 110 that would tend to deseat the tool apparatus 100. As a consequence, when unloading the tool apparatus 100 form the drive apparatus 250 it is necessary to position the drivers 256 and intermediate couplers 350 in alignment with the central line 196 to permit the tool apparatus to be removed. The alignment function may be provided by the computer controller associated with the drive apparatus 250 causing the drivers 256 to be aligned for tool apparatus removal. Additionally, the computer controller may also record and save the driver locations prior to removal of the tool apparatus so that when a new tool apparatus is inserted the controller can actuate the drivers to place the distal end 108 of the new tool in the same general location as the removed tool.

In addition, the tool apparatus 100 could also be further restrained by the retainer screw received in the opening 404 and 406. The retainer screw provides additional retaining force in the actuating direction 110 to prevent the tool apparatus 100 from sliding out of engagement with mounting interface 254. In other embodiments, the retainer screw opening may be omitted in favor of an alternative retaining mechanism, such as a detent.

In some cases, the tool apparatus 100 may be changed during a surgical procedure as necessary for the surgical operation being performed. The drive apparatus 250 may thus already be oriented so as to provide access to a surgery site on a patient and the distal end 108 of the tool manipulator 104 may be operating within the surgery site. Sliding engagement of the tool apparatus 100 within the drive apparatus 250 has an advantage of facilitating withdrawal of the tool apparatus rearwardly away from the surgery site. Similarly, when inserting a new tool apparatus 100 the distal end 108 and tool manipulator 104 are fed into the surgery site along the same path along which the previous tool apparatus was removed. The slide interface of the mounting interface 254 thus provides for simultaneous loading, engagement, and securing of the tool apparatus 100 with no secondary action associated with the loading being required other than securing the retainer screw if provided.

Another advantage associated with the tool apparatus 100 is the removal of drive components and complexity from the tool apparatus and location of these components on the chassis 252 of the drive apparatus 250. As a consequence, the tool apparatus 100 may be easier to sterilize and several units of the tool apparatus may be placed side-by-side in a trays for sterilization in an autoclave, for example. Sterile storage of the tool apparatus 100 after sterilization is also simplified. Additionally, the substantially identical drive faces 192 and 230 permit the tool apparatus 100 to be used as either a left hand side tool, or a right hand side tool. The inventory of tools that would need to be on hand is therefore minimized.

The mounting of the motor 312 extending away from the chassis 252 with respect to the tool manipulator 104 along with the mounting of the tool manipulator 104 proximate the edge 236 of the actuator housing 102, also permits two tool manipulators 104 to be operated side-by-side and in close proximity to each other.

While specific embodiments of the invention have been described and illustrated, such embodiments should be considered illustrative of the invention only and not as limiting the invention as construed in accordance with the accompanying claims.

What is claimed is:

1. A tool apparatus comprising:
    an actuator housing;
    an elongate tool manipulator extending outwardly from the actuator housing and having a plurality of control links extending along a length of the tool manipulator, the control links being operable to cause movement of a distal end of the tool manipulator in response to movement of the control links in an actuating direction generally aligned with the length of the tool manipulator;
    a plurality of actuators, each actuator being associated with at least one of the control links and being mounted in the actuator housing to facilitate a range of travel of the actuator in a transverse direction substantially orthogonal to the actuating direction of the associated at least one of the control links; and
    a plurality of linkages, each linkage being associated with one of the control links and extending between the control link and the respective actuator and being operable to transmit drive forces between the actuator and the control link.

2. The apparatus of claim 1 wherein each linkage comprises a flexible length of the respective control link and the actuator housing includes a guide associated with each linkage that causes the flexible length of the control link to be curved through a generally circular arc between the tool manipulator and the respective actuator.

3. The apparatus of claim 2 wherein the guide comprises an arcuate channel.

4. The apparatus of claim 3 further comprising a sheath covering the flexible length of the control link disposed within the channel, the sheath being operable to reduce friction between the control link and the channel.

5. The apparatus of claim 2 wherein each linkage further comprises a transition length extending in a direction generally aligned with the actuating direction, the transition length of each linkage having a length selected to cause successive ones of the plurality of actuators to be spaced along the actuator housing away from the elongate tool manipulator.

6. The apparatus of claim 2 wherein the guide comprises a pulley.

7. The apparatus of claim 1 wherein each linkage comprises a lever coupled between the associated control link and the respective actuator, the lever being operably configured to pivot in response to movement of the actuator to cause movement of the control link.

8. The apparatus of claim 1 wherein the tool manipulator comprises a rigid shaft portion and an articulated tool positioner operably configured to cause the movement of the distal end of the tool manipulator and wherein the control link comprises:
    a substantially inflexible portion extending along the rigid shaft portion; and
    a flexible portion extending through the articulated tool positioner.

9. The apparatus of claim 1 wherein the actuator housing comprises a drive face and each actuator comprises at least one drive engaging portion for receiving a drive force for moving the actuator, the at least one drive engaging portion being exposed on the drive face to facilitate coupling the actuator to a drive apparatus operable to provide the drive force.

10. The apparatus of claim 9 wherein the drive face comprises a first drive face on a side of the actuator housing and further comprising a second drive face disposed on an opposite side of the actuator housing and wherein each actuator comprises a first drive engaging portion exposed on the first drive face and a second drive engaging portion exposed on the second drive face, the first and second drive faces being operable to permit coupling of the actuator apparatus to a drive apparatus from either side of the actuator housing.

11. The apparatus of claim 1 wherein the tool manipulator extends outwardly from a portion of actuator housing proximate an edge of the actuator housing such that the length of the tool manipulator is generally aligned with the edge of the housing.

12. The apparatus of claim 1 wherein each actuator and respective linkage are configured to place the associated control links in a relaxed condition when the actuator is disposed at a location within the actuator housing that is offset from a center of the range of travel of the actuator by a small proportion of the range of travel.

13. The apparatus of claim 1 wherein the control links comprise at least one pair of control links associated with movements of the distal end of the tool manipulator in opposing directions within a common plane and wherein the actuators associated with the pair of control links are disposed in adjacent locations within the actuator housing.

14. The apparatus of claim 1 further comprising at least one tool connected to the distal end of the tool manipulator, the at least one tool providing functions controlled by at least one tool control link extending along the tool manipulator and wherein the actuator housing further comprises at least one tool actuator for controlling the at least one tool control link.

15. The apparatus of claim 14 wherein the tool control link comprises at least one of:
   a control link moveable in the actuating direction for actuating a jawed instrument and wherein the plurality of actuators and linkages include at least one actuator and a respective linkage for moving the control link in the actuating direction; and
   a tool control shaft for causing rotation of the tool about the distal end of the tool manipulator and wherein the plurality of actuators and linkages include at least one actuator and a respective linkage for transforming linear movement of the actuator into a rotating movement of the shaft.

16. The apparatus of claim 14 wherein the tool is configured to operate in response to receiving an electrical actuation signal and wherein the actuator housing further comprises:
   at least one input for receiving the electrical actuation signal; and
   a conduit extending through the housing for receiving an electrical cable for connecting the electrical signal between the input and the tool.

17. A drive apparatus for providing a drive force to actuators of a tool apparatus as claimed in claim 1, the drive apparatus comprising:
   a chassis;
   a mounting interface for receiving the tool apparatus; and
   a plurality of drivers mounted side-by-side in the chassis, each driver corresponding to one of the plurality of actuators and having a drive coupling operable to move in the transverse direction for transmitting a drive force to one of the plurality of actuators when the tool apparatus is received at the mounting interface.

18. The apparatus of claim 17 wherein each actuator of the tool apparatus comprises at least one drive engaging portion and wherein the drive coupling of each driver is exposed on the mounting interface and disposed such that drive engaging portions on the tool apparatus interconnect with corresponding drive couplings when the tool apparatus is received at the mounting interface.

19. The apparatus of claim 18 wherein each actuator and respective linkage of the tool apparatus are configured to place the associated control links in a relaxed condition when the actuator is disposed at a location within the actuator housing that is offset from a center of the range of travel of the actuator by a small proportion of the range of travel and wherein the drive coupling of each driver is disposed to cause each respective drive engaging portion of the tool apparatus to be displaced from the center of the range of travel to place the associated control links in a pre-stressed condition when the tool apparatus is received at the mounting interface.

20. The apparatus of claim 17 wherein the mounting interface comprises a slide interface configured to permit the tool apparatus to be received by sliding the actuator interface into engagement with the chassis in a direction generally aligned with the actuating direction, the drive engaging portions and corresponding drive couplings being aligned to permit the drive engaging portions to slide to interconnect with the respective drive couplings.

21. The apparatus of claim 20 wherein each drive coupling of the plurality of drivers comprises one of a protruding portion and a slot and wherein each drive engaging portion of the plurality of actuators comprises the other of a protruding portion and a slot.

22. The apparatus of claim 20 wherein the slide interface is operably configured to provide sufficient retaining force in the transverse direction to prevent de-seating of the tool apparatus when transmitting drive forces, the retaining force being provided by at least one of:
   static friction provided by contact forces between the drive engaging portions interconnecting with the corresponding drive couplings;
   actuation of at least one of the drivers causing movement of an associated drive coupling such that the plurality of drive couplings are no longer in alignment, thus preventing deseating of the tool apparatus;
   engagement of a detent operable to provide a sufficient retaining force in the actuating direction to prevent the tool apparatus sliding out of engagement with the mounting interface; and
   a fastener operable to provide a sufficient retaining force in the actuating direction to prevent the tool apparatus sliding out of engagement with the mounting interface.

23. The apparatus of claim 17 wherein each driver comprises:
   a traversing element operably configured for movement in the transverse direction; and
   a rotating element coupled to the traversing element and being operable to cause traversing element to move in the transverse direction.

24. The apparatus of claim 23 wherein the rotating element comprises a leadscrew and wherein the traversing element comprises a leadscrew nut coupled to the traversing element, the leadscrew nut being received on the leadscrew.

25. The apparatus of claim 23 further comprising a motor coupled to the rotating element for providing a rotational drive force.

26. The apparatus of claim 25 wherein the motor provides a rotational drive force to rotating elements of at least two of the drivers, and wherein the traversing elements of the at least two drivers are configured for movement in opposing transverse directions for providing opposing drive forces to respective actuators of the tool apparatus, the opposing drive forces being operable to simultaneously cause pushing of one of the control links and pulling of another of the control links.

27. The apparatus of claim 17 wherein in the event of a loss of power to the drive apparatus, each driver is operably configured to maintain the drive coupling in a generally static location with respect to the chassis to prevent unintended movement of the distal end of the tool manipulator.

28. The apparatus of claim 17 wherein the mounting interface comprises a removable barrier covering the chassis and plurality of drivers, the barrier having a plurality of intermediate couplers, the intermediate couplers being moveable in the transverse direction and being operable to transmit drive forces between the drive couplers of the drive apparatus and the respective drive engaging portions of the tool apparatus.

29. The apparatus of claim 28 wherein the removable barrier is configured to receive a sterile drape for draping the drive apparatus.

* * * * *

UNITED STATES PATENT AND TRADEMARK OFFICE
CERTIFICATE OF CORRECTION

| | |
|---|---|
| PATENT NO. | : 9,925,014 B2 |
| APPLICATION NO. | : 15/442070 |
| DATED | : March 27, 2018 |
| INVENTOR(S) | : Rene Robert |

Page 1 of 1

It is certified that error appears in the above-identified patent and that said Letters Patent is hereby corrected as shown below:

In the Specification

In Column 9 at Line 55, Change "puffing" to --pulling--.

Signed and Sealed this
Eleventh Day of June, 2019

Andrei Iancu
*Director of the United States Patent and Trademark Office*